United States Patent [19]

Allen

[11] Plant 4,446

[45] Aug. 7, 1979

[54] ORCHID PLANT

[75] Inventor: Douglas R. Allen, Jacksonville, Fla.

[73] Assignee: Fort Caroline Orchids, Inc., Jacksonville, Fla.

[21] Appl. No.: 917,027

[22] Filed: Jun. 19, 1978

[51] Int. Cl.[2] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of orchid plant of the Brassolaeliocattleya group distinguished by an overall green coloration of a large flower which has exceptional texture and substance, a robust plant growth habit, an abundant flower production, and citron scented flower smell.

1 Drawing Figure

The present invention relates to a new and distinct variety of Brassolaeliocattleya (Blc. — horticultural abbreviation) orchid plant [Blc. Ports of Paradise 'Gleneyrie's Green Giant' FCC/AOS (horticultural abbreviation) Blc. P.P. 'G.G.G.', FCC/AOS (trade abbreviation)] which was originated by me as a selected seedling derived from the hybridization on the following: *Brassavola* (B. — horticultural abbreviation) *digbyana* variety fimbripetala 'Totem Top' (unpatented, selected horticultural species) as the female parent, with Blc. Fortune 'Legacy' (unpatented) as the male parent.

The primary objective of the hybridization and breeding was to capture the green color of the female parent and the excellent shape and substance of the male parent to produce a new variety of green orchid flower, heretofore unavailable to the orchid-growing public. This objective has been fully achieved, along with other most desirable improvements, as may be evidenced by the following unique combination of characteristics which are outstanding in this new variety and distinguish it from all other varieties of which I am aware:

(1) A most robust habit of plant growth;

(2) A very large and well-shaped green orchid flower;

(3) Very abundant flower production, having flowered every month of the year at my nursery, with flowers usually borne in groups of three to five being well arranged on the stem with two to three flowering growths from the rhizome being produced at the same time;

(4) Large flower size (up to about 7¼ inches) with excellent conformation and overall coloration;

(5) Exceptional satin texture and substance of the flower petals and sepals, and the labellum has a velvety texture;

(6) A most distinctive and attractive flower in which the overall coloration is green, shading into deeper green colors within the labellum; and (7) The green coloration becomes darker with increased sun exposure unlike most other so-called "green hybrids", and the typical purple coloration on the underside of the petals as in the *B. digbyana* does not appear.

Asexual reproduction of my new orchid variety was performed for me by Brighton Farms of Linwood, N.J. by apical meristem (mericlone) process for my exclusive use. The disclosed plant has been under my exclusive control and no division of this clone has been in the possession of any person or company other than Fort Caroline Orchids, Inc., the owner and assignee of this invention, before its distribution in meristem (clonal) form in the spring of 1978.

The disclosed orchid has already received its distinction by being awarded the First Class Certificate by the American Orchid Society (FCC/AOS) on Dec. 8, 1973 at the Regional Supplemental Judging held in Atlanta, Ga., as noted on page 811 of the September 1974 American Orchid Society Bulletin and as recorded in the American Orchid Society Awards Quarterly on page 8 of Vol. 6, 1975.

The accompanying photographic drawing shows a typical flowering specimen plant as depicted in color as nearly true as is reasonably possible to reproduce by modern photographic methods; i.e., the color rendition of the photograph tends to make the flower seem more yellow than green, but the color is adequately defined hereinbelow.

The following is a detailed description of my new orchid variety, as based on specimens grown in Jacksonville, Fla., U.S.A.:

Breeding: Hybrid seedling.

*Female parent.*—*B. digbyana* variety fimbripetala 'Totem Top'.

*Male parent.*—Blc. Fortune 'Legacy'.

Propagation: By meristematic tissue culture which produces an exact copy of the original plant.

PLANT

Form: Sympodial with freely branching rhizome structure.

Blooming habit; flowering any month of the year; usually bearing three to five flowers per spike, each flower measuring about 7¼ inches in the breadth dimension.

Blooming season: Any month of the year.

Foliage:

*Leaf size.*—Length 8¾ inches. Width 2¾ inches.

*Habit.*—Upright and very robust compared to typical Cattleya varieties.

*Texture.*—Smooth.

*Edge.*—Smooth and very much razor-edged.

*Color.*—Deep green.

Psuedobulbs: Protected by several sheaths which are featured by purple on their apical portions.

*Length.*—From 8 inches to 9½ inches.

*Diameter.*—Approximately ⅞ inch.

*Distance between psuedobulbs.*—Approximately $\frac{3}{4}$ inch.

FLOWER

Carriage: In clusters of three to five per inflorescence.

Form: Border of labellum is very much fluted and closed about the column. Natural spread — about $7\frac{1}{4}$ inches.

Petals:

*Length.*—Approximately $3\frac{3}{8}$ inches.

*Width.*—Approximately $1\frac{7}{8}$ inches.

Sepals:

*Length.*—Approximately $3\frac{3}{8}$ inches.

*Width.*—Approximately $1\frac{1}{8}$ inches.

Labellum:

*Width.*—Approximately $3\frac{1}{2}$ inches.

Color of flower: Referenced by Exotica Horticultural Color Guide, Copyright by Roehrs Company 1962, Rutherford, N.J., U.S.A.

*Tepals.*—Concolor No. 79 Citron.

*Labellum.*—Border is No. 79 Citron, shading into deeper tones of No. 80 Nile Green in the central throat thereof.

Smell: Heavy citron scented.

I claim:

1. A new and distinct variety of Brassolaeliocattleya orchid plant substantially as herein shown and described characterized particularly as to novelty by the unique combination of a substantially concolor green flower, abundant year around flower production, with flowers being well displayed and of very heavy substance, lasting for about a full month in a cool atmosphere, and the flower having a heavy citron scent.

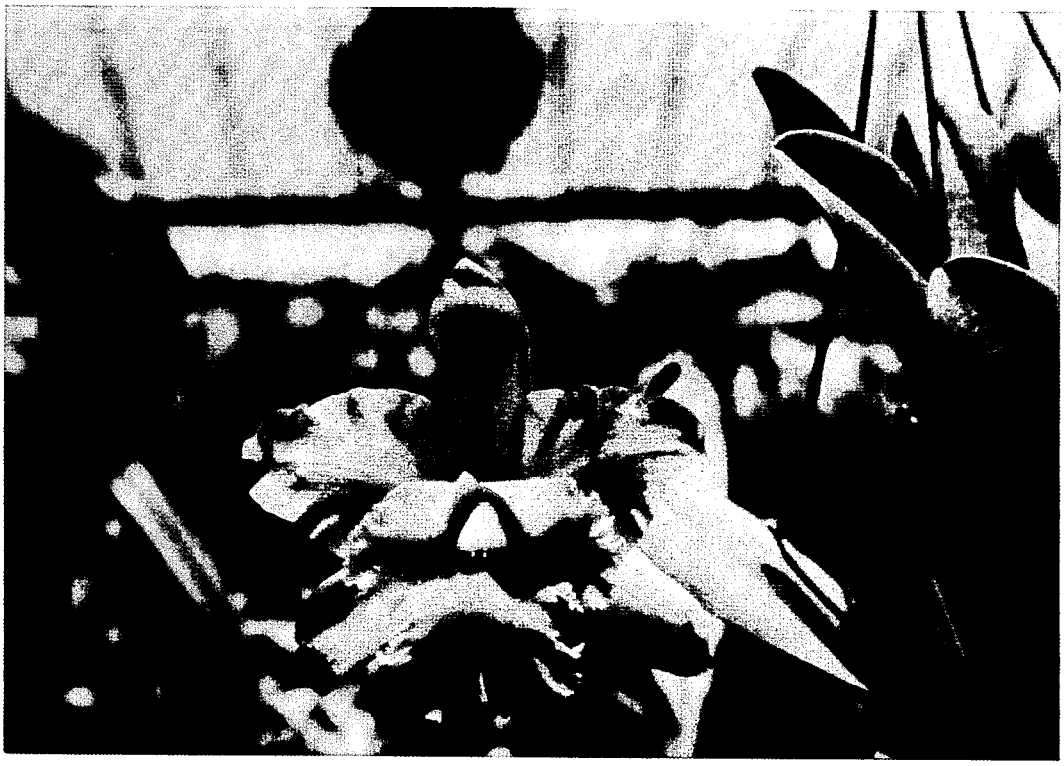

* * * * *